United States Patent [19]
Raneri et al.

[11] Patent Number: 5,849,186
[45] Date of Patent: Dec. 15, 1998

[54] INTEGRATED CARDIOTOMY AND VENOUS BLOOD RESERVOIR

[75] Inventors: Joseph J. Raneri, Tewksbury; Kenneth E. Buckler, Methuen; Charles L. Stanley, Amesbury, all of Mass.; Alfred P. Intoccia, Eden Prairie, Minn.

[73] Assignee: C. R. Bard Inc., Murray Hill, N.J.

[21] Appl. No.: 749,432

[22] Filed: Nov. 15, 1996

[51] Int. Cl.⁶ .......................... B01D 19/02; B01D 36/00
[52] U.S. Cl. .......................... 210/315; 96/179; 210/338; 210/436; 210/483; 210/489; 604/4; 604/406; 422/45; 264/45.1
[58] Field of Search ...................... 210/188, 314, 210/315, 337, 338, 436, 438, 446, 451, 455, 456, 472, 483, 488, 489, 490, 492, 645; 604/4, 317, 403, 406; 422/44–48; 95/242, 287; 96/176, 179

[56] References Cited

U.S. PATENT DOCUMENTS

| | | |
|---|---|---|
| 3,898,045 | 8/1975 | Bowley . |
| 4,058,369 | 11/1977 | Bentley et al. . |
| 4,073,622 | 2/1978 | Luppi . |
| 4,228,125 | 10/1980 | Lobdell et al. .......................... 422/46 |
| 4,261,951 | 4/1981 | Milev .......................... 422/46 |
| 4,451,562 | 5/1984 | Elgas et al. .......................... 422/46 |
| 4,818,490 | 4/1989 | Carson et al. .......................... 422/46 |
| 5,127,900 | 7/1992 | Schickling .......................... 210/436 |
| 5,158,533 | 10/1992 | Strauss et al. .......................... 604/4 |
| 5,167,921 | 12/1992 | Gordon .......................... 210/492 |
| 5,411,705 | 5/1995 | Thor et al. .......................... 210/436 |
| 5,458,567 | 10/1995 | Cathcart .......................... 604/4 |

FOREIGN PATENT DOCUMENTS

| | | | |
|---|---|---|---|
| 371173 | 6/1990 | European Pat. Off. .......................... | 604/406 |

*Primary Examiner*—Joseph W. Drodge
*Attorney, Agent, or Firm*—Pillsbury Madison & Sutro LLP

[57] ABSTRACT

A blood reservoir for the treatment and collection of blood from two different sources. The blood reservoir has a filter/defoamer core assembly comprised of a support structure disposed within an outer defoamer. A separator with an opening is located in the support structure, dividing the support structure into a first and second portions. A depth filter is located within the first portion of the support structure. The first portion of the support structure with the depth filter forms a cardiotomy blood chamber and the second portion with no depth filter forms a venous blood chamber. This filter/defoamer core assembly is placed within a clear outer shell which forms the reservoir. This outer shell has a cover with a venous blood inlet and plurality of cardiotomy inlets. The cardiotomy inlets are in fluid communication with the cardiotomy blood chamber. The venous blood inlet is in communication with a center tube which extends through the first portion of the support cage, through the opening in the separator and opens into the venous blood chamber. The filter/defoamer core assembly may be assembled and positioned within the reservoir shell without the use of adhesives or bonding agents. This blood reservoir is typically used in a system including components to oxygenate and alter the temperature of the blood.

40 Claims, 8 Drawing Sheets

INTEGRATED CARDIOTOMY AND VENOUS BLOOD RESERVOIR

BACKGROUND OF THE INVENTION

The invention relates to a new and improved integrated cardiotomy and venous blood reservoir device, and more specifically to such a device which is compact, provides for ease of assembly, and improved filtration. Further embodiments relate to methods of manufacturing the reservoir device and systems employing the reservoir device and a blood oxygenator/heat exchanger.

Blood reservoirs are well recognized in the prior art. Blood reservoirs are commonly used, for example, during open heart surgery by a perfusionist and are coupled to a cardiopulmonary bypass circuit which takes over the function of the heart and lungs. The blood reservoir stores and filters blood in the bypass circuit.

Cardiotomy blood comes from the surgery situs or chest cavity, and often includes debris such as bone chips, saline solution, and liquids applied to the heart. The cardiotomy blood must be filtered before being returned to the patient. Venous blood comes directly from the vena cava or right atrium and does not include the debris found in cardiotomy blood. Venous blood does not require filtration. Defoamers are used with both the venous and cardiotomy blood to remove foam from the blood.

Defoamers and filters are commonly used with blood reservoirs to filter particulate material and foam from the blood. In recent years, the cardiotomy and venous reservoir components have been combined in a single unit which requires separate chambers for the cardiotomy and venous blood. Examples of such integrated devices are described in U.S. Pat. Nos. 4,642,089 and 5,158,533.

Integrated cardiotomy/venous blood reservoirs are often used by a perfusionist in an extra-corporeal blood circuit during such surgical procedures as open heart surgery to store, trap air, and filter blood. During arterial incapacitation, the blood is transferred and stored in a reservoir. The cardiotomy portion of the reservoir holds and filters blood salvaged from the patient's chest cavity or surgery situs. The venous portion of the reservoir holds and filters blood directly from the right atrium or vena cava. The cardiotomy portion must provide more filtration than the venous portion because blood transferred from the chest cavity often contains debris such as bone pieces, skin, etc. Blood from the vena cava typically requires less filtration than cardiotomy blood salvaged from the chest cavity because venous blood is not contaminated with debris from the surgery situs.

SUMMARY OF THE DISCLOSURE

It is an object of preferred embodiments of the present invention to integrate the cardiotomy and venous reservoir and filtration components in a single unit and at the same time provide more filtration for the cardiotomy component. It is a further object to provide an improved structure and method of manufacturing the cardiotomy and venous blood chambers and providing separation therebetween. It is still a further object to assemble a filter/defoamer core assembly and affix the filter/defoamer assembly within the reservoir without using any adhesives or bonding chemicals.

These and other objects and advantages are achieved in an integrated cardiotomy and venous blood reservoir wherein a generally cylindrical, hollow support structure separated by a separator disposed within the support structure is used to form both a cardiotomy chamber and venous blood chamber. The support structure has a first end, a second end, and a wall therebetween with an aperture in the wall. The axial length of the support structure is divided into a first portion extending from the first end along the axial length, and second portion extending the remaining axial length to the second end. Preferably, the support structure is a generally cylindrical, hollow cage having ribs extending the axial length of the generally cylindrical structure.

The support structure is disposed within a generally cylindrical, hollow blood defoamer which extends along the first and second portions of the support structure. Preferably a fabric sock extends around the outer defoamer to maintain the outer defoamer compressed against the support structure. A separator with an opening is disposed within the support structure and is located between the first and second portions of the support structure. In a preferred embodiment a generally cylindrical, hollow depth filter is disposed within the support structure, between the first end and the separator. However, in alternative embodiments, the support structure may be disposed within the depth filter or both the outer defoamer and depth filter may be disposed within the support structure. Further, a first inner defoamer may be disposed within the depth filter in the first portion of the support structure and a second inner defoamer may be disposed within the second portion of the support structure. In preferred embodiments, the inner defoamer disposed within the second portion of the support structure is part of the outer defoamer wrapped around the second end of the support structure.

A tube extends axially through the first portion of the support structure, through the opening in the separator and into the second portion of the support structure. One end of the tube is in fluid communication with the outer defoamer in the second portion of the support structure, or in fluid communication with a second inner defoamer disposed within the second portion of the support structure the if there is such a second inner defoamer.

In preferred embodiments, the support structure, defoamer, filter, separator and tube, are disposed within a generally cylindrical, hollow outer shell having a first end, a second end, and a wall therebetween, wherein the outer defoamer is spaced apart from the annular wall of the outer defoamer. A first blood inlet and a second blood inlet are located on the first end of the outer shell, and a blood outlet is located on the outer shell. Preferably, the first end is comprised of a cover which is bonded to the wall of the shell. The tube is in fluid communication with the first blood inlet and the second blood inlet is in fluid communication with the depth filter.

In this way, a cardiotomy chamber is formed by the separator, depth filter, and inner defoamer in the first portion of the support structure. Thus, the second blood inlet, which is in fluid communication with the depth filter, functions as a cardiotomy blood inlet. A venous blood chamber is formed by the separator and defoamer in the second portion of the support structure. The first blood inlet in communication with the tube functions as a venous blood inlet.

In preferred embodiments, a deflector having an opening is located between the first end of the support structure and the first end of the outer shell. The tube extends from the first blood inlet through the opening in the deflector. The deflector guides blood from the second blood inlet into the cardiotomy chamber.

Embodiments of the present invention are also directed to methods of manufacturing the above apparatus. The filter/defoamer core assembly is formed by first disposing the support structure within the outer defoamer. Preferably, a fabric sock is then placed around the outer defoamer to maintain the outer defoamer compressed against the support structure. The depth filter is then placed in the first portion of the support structure. The separator is then placed in the support structure, between the first and second portions of the support structure. The first and second inner defoamers may then be placed within the first and second portions of the support structure, respectively.

The tube for communication with the first blood inlet is then inserted through the first portion of the support structure, through the opening in the separator, and into the second portion of the support structure. The tube is then affixed to the first end of the outer shell to be in fluid communication with the first blood inlet. The first end of the outer shell is then affixed to the outer shell. In this way, the filter/defoamer core assembly may be manufactured without the use of adhesives or other bonding chemicals.

DETAILED DESCRIPTION OF PREFERRED EMBODIMENTS

FIGS. 1–6 show preferred embodiments of an integrated venous/cardiotomy blood reservoir 4 and a system composed of the integrated venous/cardiotomy blood reservoir 4 and an integrated oxygenator/heat exchanger 2. In the detailed description below, references made to the "top," "bottom," "upper," or "lower" portions of the blood reservoir 4, or elements thereof, are made with reference to the orientation of the structures shown in the drawings and are not intended to limit the scope of the invention where such limitations are not otherwise required.

Figure 1:
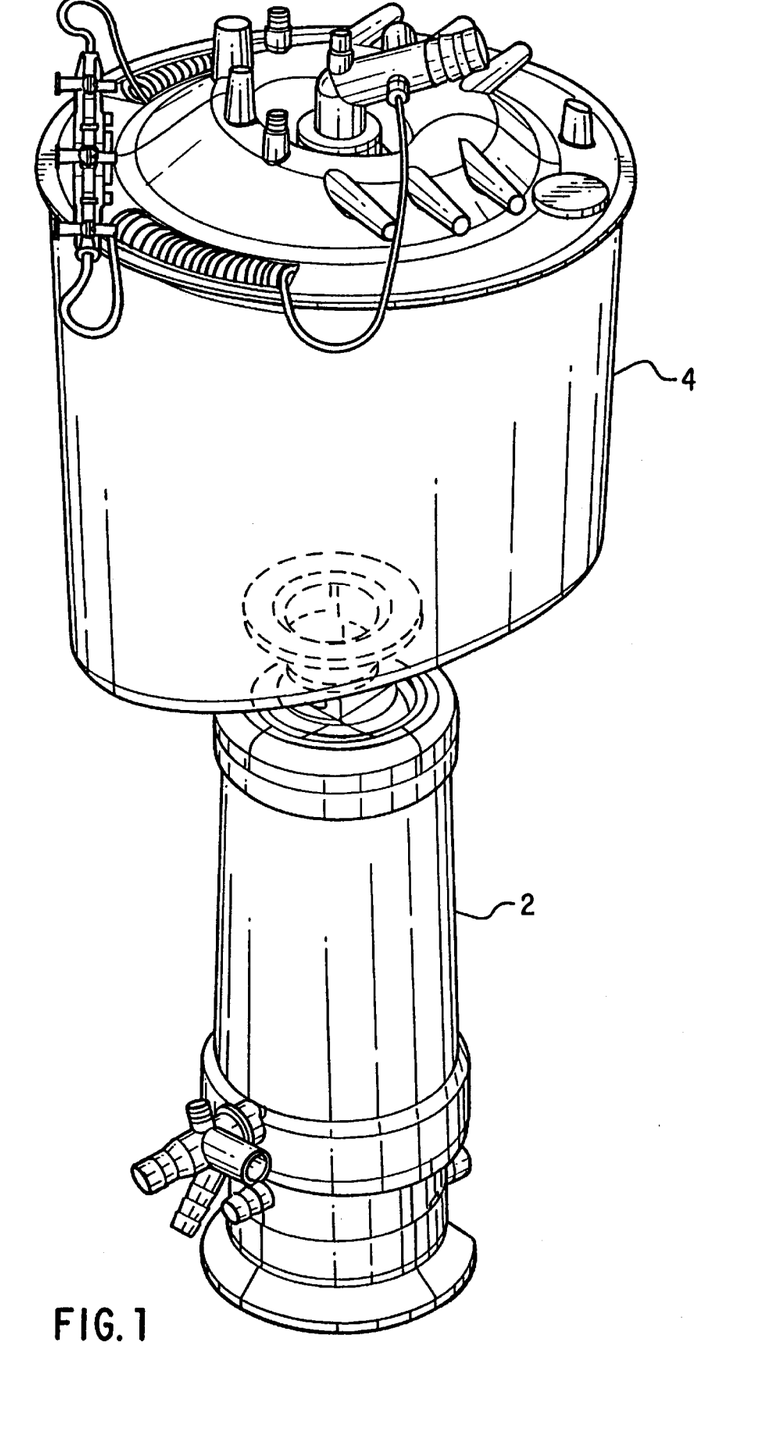
FIG. 1 is a perspective view showing an embodiment of a system composed of an integrated venous and cardiotomy reservoir and an integrated oxygenator/heat exchanger.

As shown in the system embodiment of FIG. 1, the venous/cardiotomy reservoir 4 is preferably used in combination with a membrane oxygenator and heat exchanger 2 which receives blood transferred from the reservoir 4 and oxygenates and alters the temperature of the blood. Preferably, the membrane oxygenator/heat exchanger 2 is of the type described in the U.S. Pat. application Ser. No. 08/744,869 titled Integrated Oxygenator and Heat Exchanger, filed under U.S. Express Mail label no. EM419214600US, on Nov. 7, 1996, (incorporated herein by reference) and assigned to the assignee of the present invention. However, other suitable oxygenators or integrated oxygenator/heat exchangers may be used with the reservoir 4 in other system embodiments. In preferred embodiments, blood reservoir 4 is a single use reservoir for intraoperative perfusion of adult patients. From the reservoir 4, filtered blood is then transferred to the oxygenator/heat exchanger 2 via tubing (not shown). A pump, such as a peristaltic pump (not shown), may be applied to the tubing connecting the blood reservoir 4 and oxygenator/heat exchanger 2. The pump is preferably controlled to provide the blood at a desired pressure to the oxygenator/heat exchanger 2. The reservoir 4 is preferably positioned higher than the heat exchanger/oxygenator 2 to maintain positive pressure on the oxygenator when blood flow is stopped.

Figure 2:
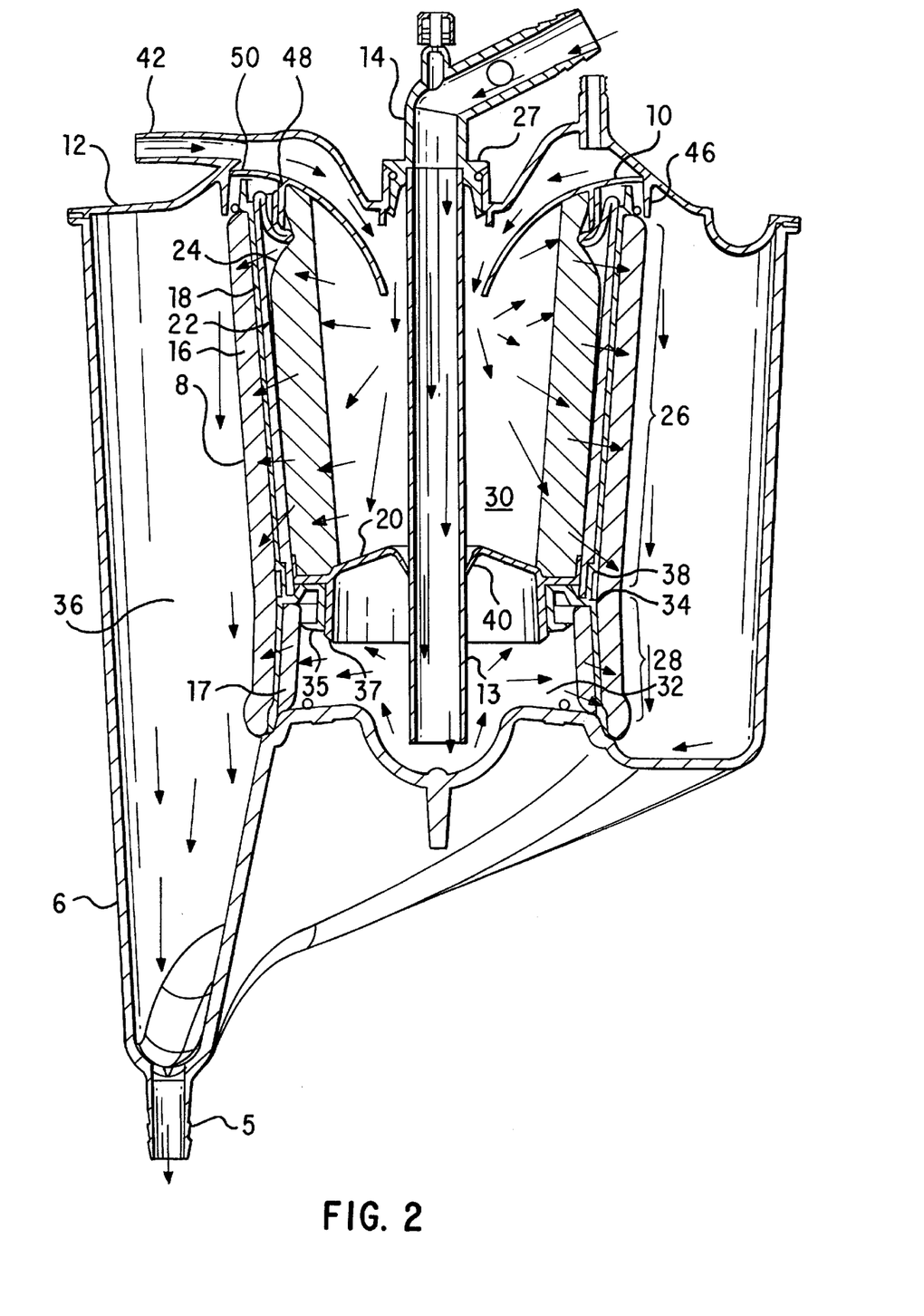
FIG. 2 is a cross sectional diagram of the integrated venous and cardiotomy reservoir of FIG. 1.
Figure 3:
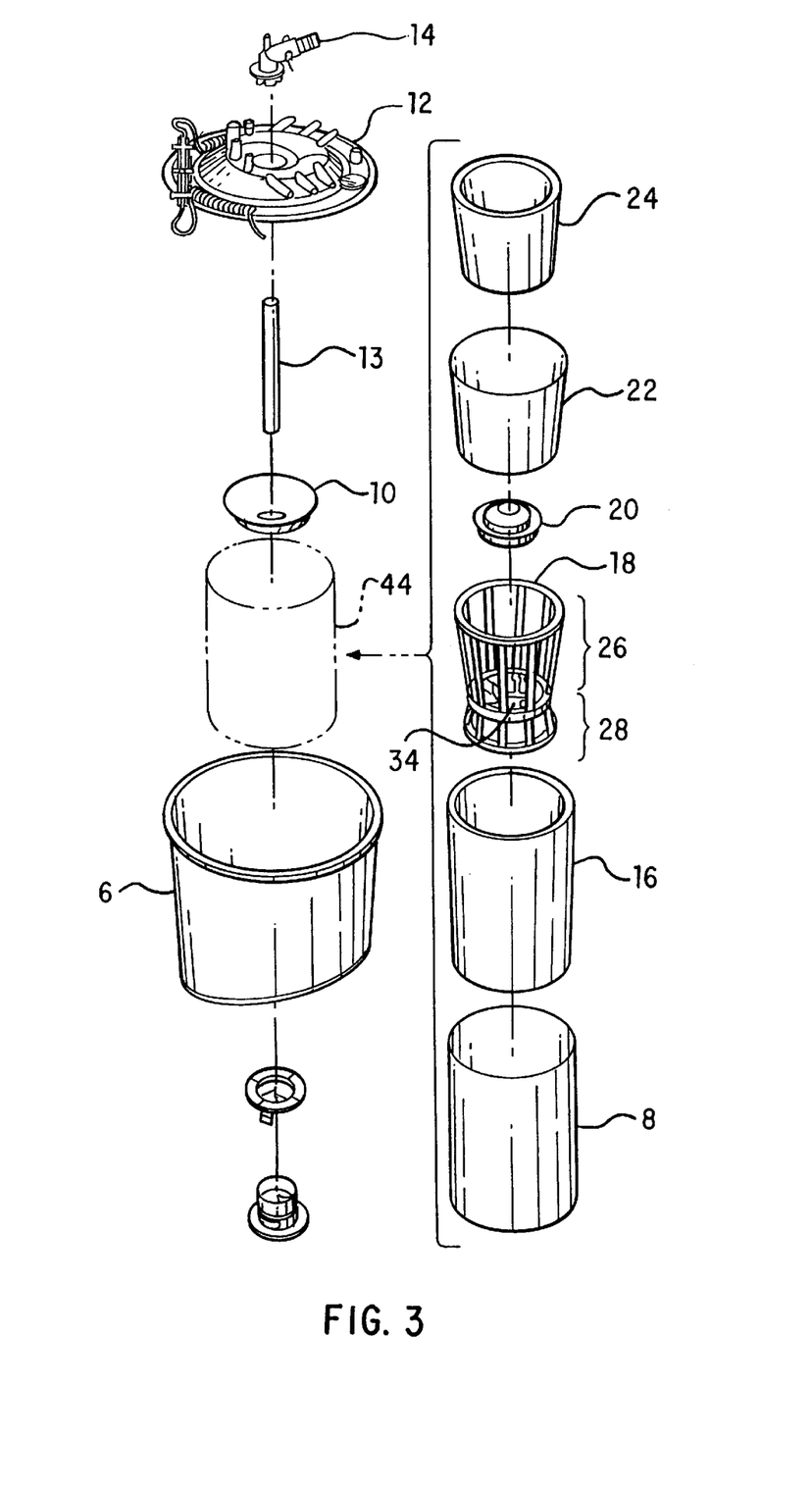
FIG. 3 is an exploded layout of a preferred embodiment of the integrated venous cardiotomy reservoir of FIG. 1.

A preferred embodiment of the blood reservoir is described with reference to FIGS. 2–6. Referring to FIGS. 2 and 3, the venous/cardiotomy blood reservoir 4, when assembled, can be characterized as comprising six concentric shells, each shell having a substantially cylindrical shape. The innermost shell is a generally cylindrical, hollow inner defoamer 24. The second shell is a generally cylindrical, hollow depth filter 22. The third shell is a generally cylindrical, hollow support structure 18, wherein the axial length of the support structure 18 has an upper first portion 26 and a lower second portion 28. The inner defoamer 24 and depth filter 22 each extend the length of the first portion 26 of the support structure 18. The fourth shell is a generally cylindrical, hollow outer defoamer 16. The fifth shell is a fabric sock 8. The sixth shell is a generally cylindrical, hollow outer shell 6.

Figure 6:
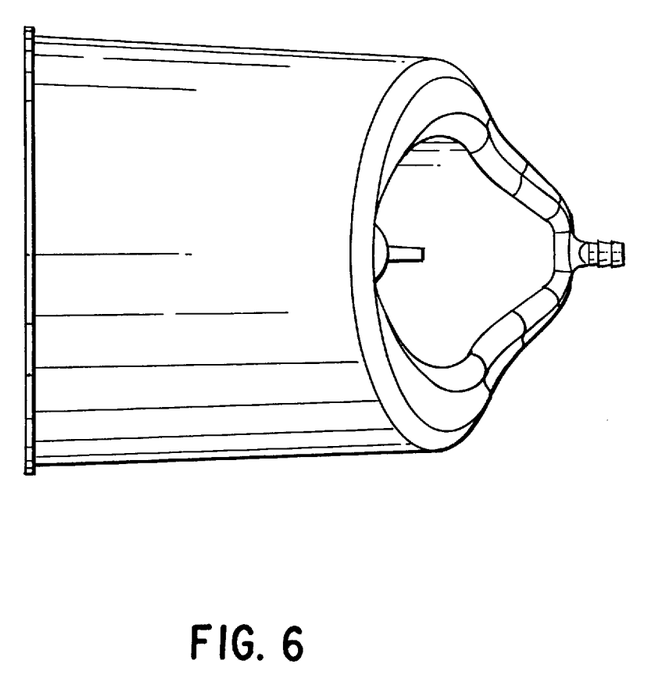
FIG. 6 is a side view of a preferred embodiment of the outer shell of the blood reservoir.

FIGS. 2 and 6 show a preferred embodiment of the outer shell 6. The lower end of the outer shell 6 inverts upward in the center thereby forming an annular funnel channel converging downward toward one side of the shell. At the lower most point of the annular funnel of the shell 6 is a blood outlet 5. With reference to FIG. 2, a blood flow channel 36 is formed between the outer shell 6 and the outer defoamer 16, which may be covered by the fabric sock 8. In a preferred embodiment, the outer shell 6 is made of a clear, injection molded polycarbonate and is not taller than about sixteen inches. The blood flow channel 36 is visible to the perfusionist or user of the reservoir, through the outer shell 6. It should be appreciated that alternative shapes or sizes of the outer shell 6 may be used, and that the outer shell may be comprised of any suitable material. Further, the blood outlet 5 may be placed at other locations on the outer shell 6 than that shown in the preferred embodiment shown in the drawings.

The depth filter 22 is comprised of a material having a density greater than the density of the inner and outer defoamers 24, 16. The depth filter 22 and defoamers 24, 16 are preferably comprised of polyester or polyurethane materials well known in the art. In a preferred embodiment, the depth filter is disposed within the first portion of the support structure. However, it should be appreciated that, in alternative embodiments, the depth filter 22 may be located on the outside surface of the support structure or both the outer defoamer 16 and depth filter 22 may be disposed within the support structure 18. In preferred embodiments, the hollow inner defoamer 24 is disposed within the depth filter 22. Alternatively, the inner defoamer 24 may be comprised of a sponge defoaming material that fills the space formed within the annular depth filter 22.

Figure 4A:
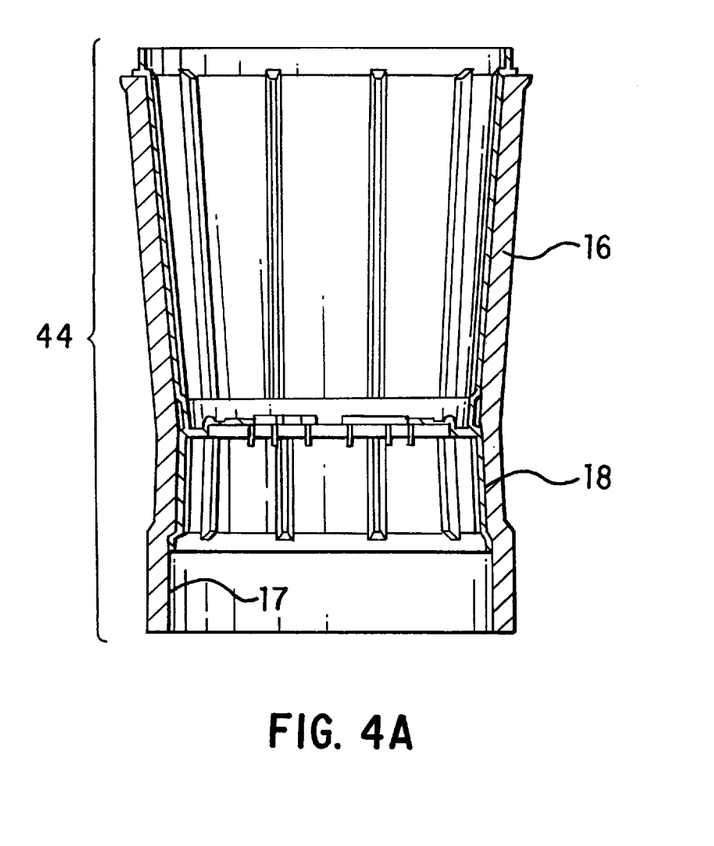
FIGS. 4a, 4b, 4c, 4d are different cross-sectional views of a preferred embodiment of the filter/defoamer core assembly.
Figure 4B:
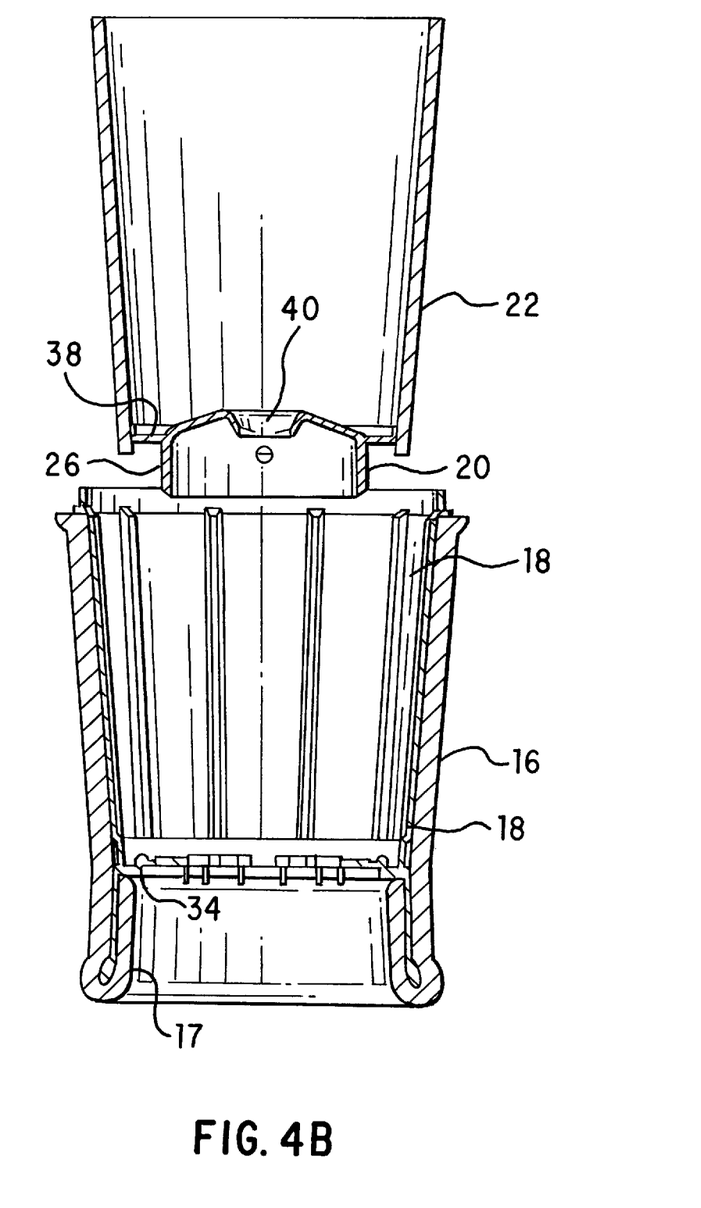
Figure 4C:
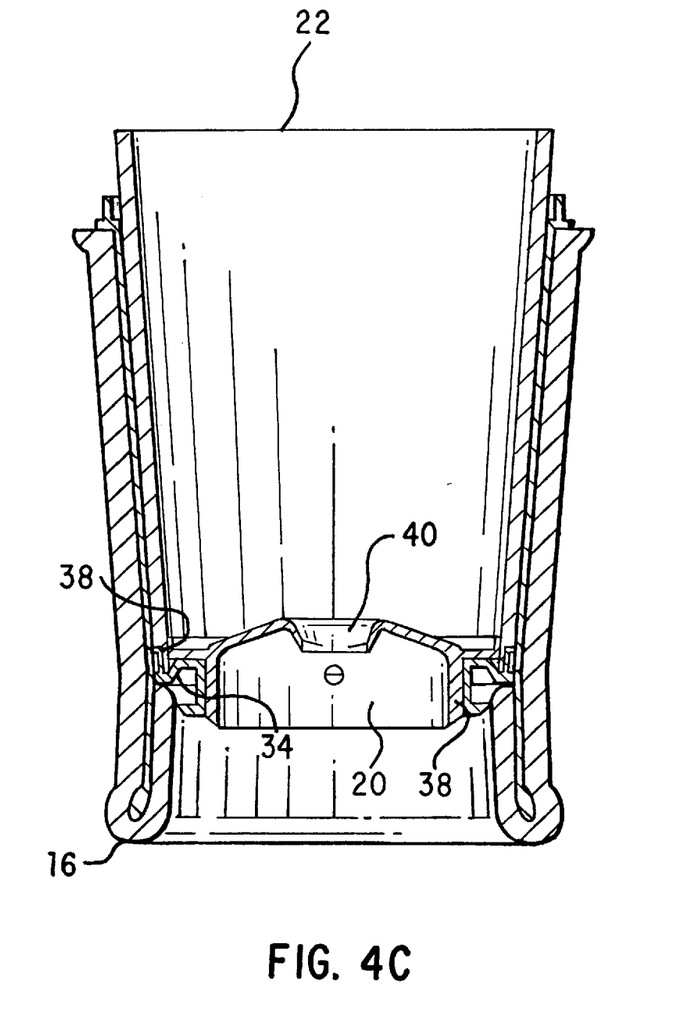

The support structure 18 provides support for the filters and defoamers. The support structure 18 may be formed of a polyolefin or other thermoplastic material. With reference to FIGS. 3, 4a, and 4b, the support structure 18 has an upper first end and a lower second end. In preferred embodiments, the support structure is a generally cylindrical, hollow cage having a plurality of axial ribs extending the axial length of the cage. In should be appreciated that alternative shapes or designs of the support 18 may be provided. For instance, the support structure 18 may be comprised of a generally cylindrical, hollow wall with a plurality of apertures or may have a non-cylindrical shape. With reference to FIGS. 2 and 3, the first portion 26 of the support structure 18 defines a cardiotomy blood chamber 30 and the second portion 28 defines a venous blood chamber 32.

With reference to FIGS. 2 and 4a–d, the inner surface of the support structure 18 has an annular dividing ledge 34 located between the first and second portions 26, 28. In preferred embodiments shown in FIGS. 4b, 4c, and 4d, a separator 20, has an upper flange 38, a lower flange 37, and a center opening 40. The separator 20 and depth filter 22 are disposed within the support structure 18. The upper flange 38 of the separator 20 rests on the dividing ledge 34 and compresses the depth filter 22 against the support structure 18. In this way, separator 20, support structure 18, and filter 22, compressed between the separator 20 and support structure 18, form a separate dividing wall separating the first and second portions 26, 28 of the support structure 18 to define separate cardiotomy 30 and venous 32 blood chambers.

Figure 4D:
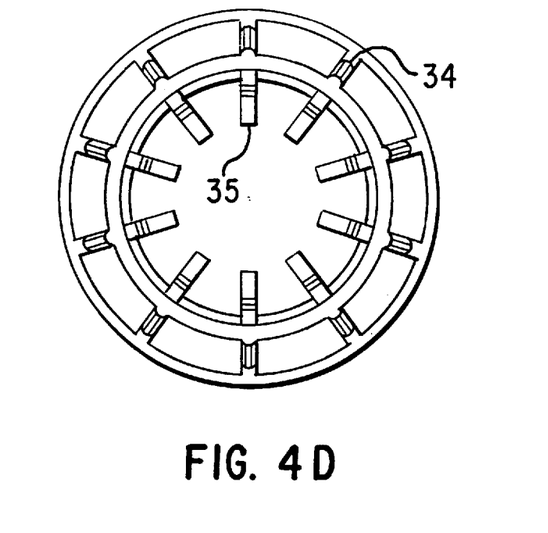

FIG. 4d shows a plurality of bendable tabs 35 attached to the annular dividing ledge 34 that extend toward the center of the support structure 18. When the separator 20 is inserted in the support structure and the upper flange 38 rests on the dividing ledge 34, the tabs 35 extend between the upper flange 38 and lower flange 37 of the separator 20 to firmly maintain the separator 20 and the inner section 17 of the outer defoamer 16 in place.

It should be appreciated that alternative structures may be used to separate the cardiotomy 30 and venous 32 chambers or bonding agents may be used to maintain the separator in place.

In preferred embodiments, the outer defoamer 16 extends the axial length of the support structure 18. With reference to FIGS. 2 and 4a–c, a lower end 17 of the outer defoamer 16 wraps around the bottom end of the support structure 18 and extends upward the length of the second portion 28 to the separator 20. It should be appreciated that in alternative embodiments the defoamer on the inside surface of the venous chamber 32 may be comprised of a separate defoamer instead of being a portion 17 of the outer defoamer 16 that wraps around the bottom of the support structure 18. The inner defoamer in the second portion may be a generally cylindrical, hollow defoamer or a defoaming sponge that fills the second portion of the venous chamber 32. The fabric sock 8 (FIGS. 2 and 3) extends around the outer defoamer 16 and maintains the defoamer 16 positioned against the support structure 18.

In this way, the cardiotomy chamber 30 is bounded by the inner defoamer 24, the depth filter 22, the outer defoamer 16, and the fabric sock 8. The lower venous chamber 32 is bounded only by the outer defoamer 16 doubled over. The cardiotomy chamber 30 preferably includes the additional layer of the depth filter 22 because more debris is typically present in blood from the chest cavity or surgery situs than in venous blood that goes to the venous chamber 32.

Figure 5A:
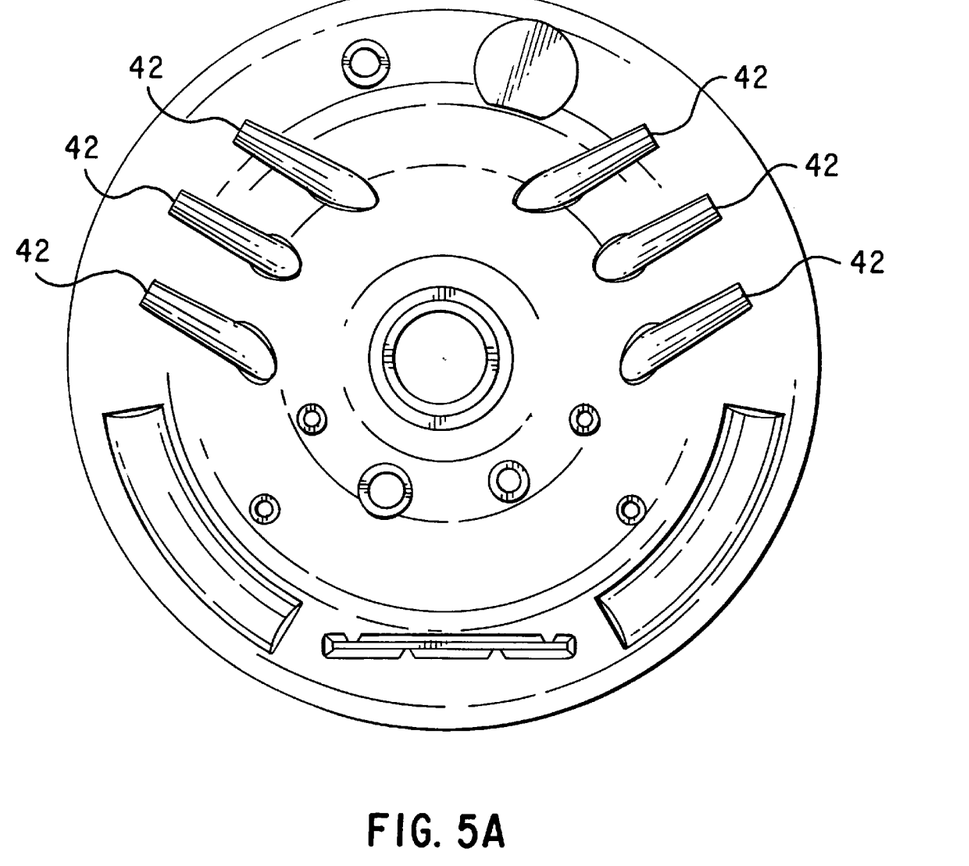
FIGS. 5a and 5b are top and side views, respectively, of a preferred embodiment of the cover.
Figure 5B:
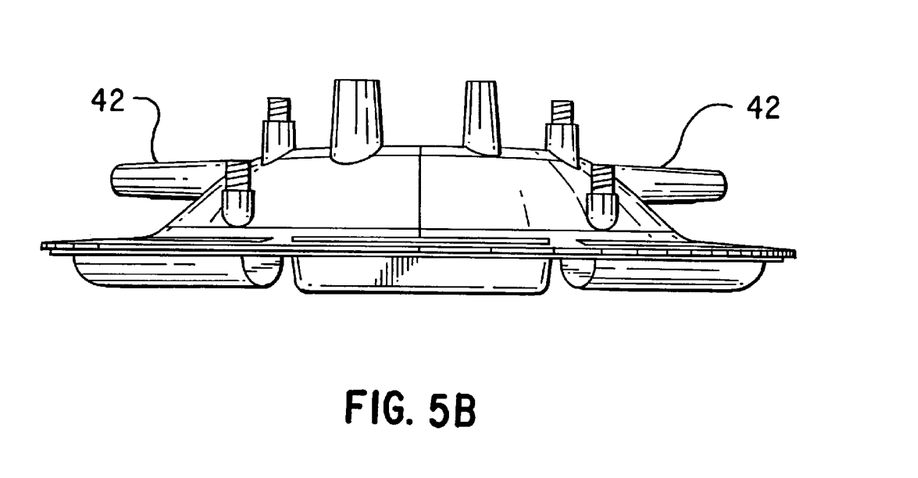

A preferred embodiment of a cover 12 is shown in FIGS. 2, 3, and 5. The cover 12 is attached to the top end of the outer shell 6 by bonding, welding or other suitable attachment means. FIG. 5a shows the cover having six cardiotomy inlets 42 that open laterally into the deflector 10. FIG. 5a shows an embodiment of the cover 12 having additional inlets, leurs, and vents used to sample blood, introduce medication, or vent trapped air.

A funnel-shaped deflector 10 is located between the first end of the support structure and the cover. The deflector 10 is in fluid communication with the second blood inlets 42 and the cardiotomy chamber 30.

With reference to FIGS. 2 and 3, a venous center tube 13 extends downward from the center opening in the cover 12, through the center opening in the deflector 10, through cardiotomy chamber 34, through the center opening 40 in the separator 20, and into the venous chamber 32. In preferred embodiments, the venous center tube 13 opens near the bottom of the venous chamber 32. A venous inlet 14 is attached to the cover 12 and is in fluid communication with the upper end of the venous center tube 13. The venous inlet 14 is adapted to be linked with a line (not shown) to the vena cava or right atrium of a patient's heart.

In operation, with reference to FIG. 2, venous blood travels from a line connected to the right atrium, through the venous inlet 14, through the venous center tube 13 and into the venous chamber 32. Venous blood then flows laterally through the wrapped around portion 17 of the outer defoamer 16 and through the main portion of the outer defoamer 16 into the blood flow channel 36. The filtered venous blood then exits the reservoir through the blood outlet 5.

With reference to FIG. 2, cardiotomy blood from the surgery situs travels from a line (not shown) to the cardiotomy inlets 42. Blood flows through the inlets to the deflector 10, which directs the blood into the cardiotomy chamber 30 along the outside of the venous center tube 13. Cardiotomy blood then flows laterally through the inner defoamer 24, through the depth filter 22, through the support structure 18, and then through the outer defoamer 16, through the fabric sock 8, and into the blood flow channel 36. The filtered cardiotomy blood then exits the reservoir through the blood outlet 5.

As described in detail above, preferred embodiments of the present invention provide a compact housing integrating both the cardiotomy and venous blood reservoir components within a single support structure. The integrated housing provides an additional layer of filtration for the cardiotomy blood. In this way a higher level of filtration of the cardiotomy blood is performed, while at the same time minimizing trauma to the venous blood which typically needs less filtration than cardiotomy blood.

Embodiments of the present invention are designed to provide improvements and benefits with respect to the ease of manufacture. In preferred embodiments, a filter/defoamer core assembly 44 is manually assembled as shown in FIGS. 3 and 4a–c, where the support structure 18 is placed within the annular outer defoamer 16. The sock 8 is then placed over the outer defoamer 16 to maintain the defoamer 16 in contact with the support structure 18. As shown in FIG. 4b, the separator 20 and depth filter 22 are then placed into the first portion 26 of the support structure 18. The separator 20 is placed in the depth filter 22 and positioned to rest on the dividing ledge 34. The separator 20 compresses an end of the depth filter 22 against the support structure. The inner defoamer 24 is then placed within the hollow depth filter 22. It should be appreciated that steps of the manufacture of the filter/defoamer core assembly 44 may be performed with automation. In addition, in preferred embodiments, the filter/defoamer core assembly 44 is assembled without the use of adhesives or bonds. In this way, the filter core may be manually assembled quickly, in a cost effective manner.

In preferred embodiments shown in FIGS. 2 and 3, the inner defoamer 24, depth filter 22, and the first portion of the support structure 26 are tapered toward the bottom. Accordingly, the lower part of these generally, hollow shell components has a circumference that is less than the upper part of the element in which they are being placed. The tapered shape makes it easier to insert the generally cylindrical shell components 24, 22, and 26 one inside the other.

As part of the manufacturing process, the venous center tube 13 is bonded to the venous blood inlet 14. The blood inlet 14 is snapped into the cover 12. An o-ring 27 may be used to provide rotational resistance between the blood inlet 14 and the opening in the cover 12, which seals the cardiotomy section 30. In preferred embodiments, the cover 12 has an annular wall 46 and the deflector 10 also has an annular wall 48. The funnel-shaped deflector 10 is inserted into the space formed by the annular wall 46 of the cover 12 and maintained in place by means of a compression fit with the annular wall 46. The filter/defoamer 44 core assembly is then placed in a channel 50 formed between the annular wall 46 of the cover 12 and the annular wall 48 of the deflector 10. When the filter/defoamer core assembly 44 is positioned with respect to the cover 12, the venous center tube 13 extends through the center opening of the deflector 10 and the center opening of the separator 20. The cover 12 is then bonded to the open end of the outer shell 6.

In preferred embodiments, the components of the filter/defoamer core assembly 44 are not bonded with adhesives or bonds to the shell 6, but are instead maintained in place with a tight fit with the outer shell 6 and annular walls 46 and 48 extending from the cover 12 and deflector 10. In preferred embodiments, the venous portion of the reservoir is capable of handling blood flow rates of one to seven liters per minute. The cardiotomy portion is capable of handling blood flow rates of one to five liters per minute and the combined venous/cardiotomy components can handle blood flow rates of one to seven liters per minute.

We claim:

1. An integrated cardiotomy and venous blood reservoir and oxygenator system for use in an extracorporeal circuit, comprising:

a blood reservoir comprising:

(a) a generally cylindrical, hollow outer shell having a first end, a second end, and a wall extending from the first end to the second end;

(b) a first blood inlet;

(c) a second blood inlet;

(d) a generally cylindrical, hollow shaped outer blood defoamer disposed within the outer shell and spaced apart from the wall of the outer shell, wherein the outer blood defoamer is in fluid communication with the first and second blood inlets;

(e) a blood outlet in fluid communication with the outer blood defoamer;

(f) a unitary, generally cylindrical, hollow support structure having a first end, a second end, a generally cylindrical wall extending without interruption from the first to the second end, and an aperture within the wall, wherein the axial length of the support structure is comprised of a first portion and a second portion, wherein the first portion extends from the first end of the support structure along a portion of the axial length and the second portion extends the remaining portion of the axial length to the second end, and wherein the support structure is disposed within the outer defoamer;

(g) a separator disposed within the support structure and located between the first and second portions of the support structure, wherein the first blood inlet is in fluid communication with the separator and second portion of the support structure; and (h) a generally cylindrical, hollow depth filter disposed within the first portion of the support structure, wherein the second blood inlet is in fluid communication with the depth filter, and wherein the depth filter is in fluid communication with the outer defoamer; and a blood oxygenator which receives blood from the blood outlet of the blood reservoir.

2. An integrated cardiotomy and venous blood reservoir, comprising:

a hollow outer shell having a first end, a second end, and a wall extending from the first end to the second end;

a first blood inlet;

a second blood inlet;

a hollow shaped outer blood defoamer disposed within the outer shell and spaced apart from the wall of the outer shell, wherein the outer blood defoamer is in fluid communication with the first and second blood inlets;

a blood outlet in fluid communication with the outer blood defoamer;

a unitary, hollow support structure having a first end, a second end, a wall extending without interruption from the first to the second end, and an aperture within the wall, wherein the axial length of the support structure is comprised of a first portion and a second portion, wherein the first portion extends from the first end of the support structure along a portion of the axial length and the second portion extends the remaining portion of the axial length to the second end, and wherein the support structure is disposed within the outer defoamer;

a separator disposed within the support structure and located between the first and second portions of the support structure, wherein the first blood inlet is in fluid communication with the separator and second portion of the support structure; and a depth filter disposed within the first portion of the support structure, wherein the second blood inlet is in fluid communication with the depth filter, and wherein the depth filter is in fluid communication with the outer defoamer.

3. The blood reservoir of claim 2, wherein the support structure is comprised of a cage having a plurality of ribs extending along the axial length of the support structure.

4. The blood reservoir of claim 2, wherein the outer shell, outer blood defoamer, support structure, and depth filter have a generally, cylindrical shape.

5. The blood reservoir of claim 2, wherein the support structure is disposed within the depth filter and wherein the depth filter surrounds the first portion of the support structure.

6. The blood reservoir of claim 2, wherein the outer defoamer and depth filter are disposed within the support structure.

7. The blood reservoir of claim 2, wherein the depth filter is hollow and wherein the first portion of the support structure and depth filter are tapered toward the end adjacent to the separator.

8. The blood reservoir of claim 2, wherein a portion of the second end of the outer shell inverts toward the first end of the outer shell thereby forming an annular funnel channel at the second end, wherein the annular funnel channel converges downward toward one side of the shell, wherein the blood outlet is located at the point where the funnel channel converges.

9. The blood reservoir of claim 2, wherein the outer shell, including first end, second end, and outer shell wall are formed from a plurality of components coupled together.

10. The blood reservoir of claim 2, wherein the-outer shell is comprised of a clear, generally transparent material.

11. The blood reservoir of claim 2, wherein a fabric extends around the outer defoamer to maintain the outer defoamer compressed against the support structure.

12. The blood reservoir of claim 2, further including an inner defoamer disposed within the depth filter and in fluid communication with the second blood inlet.

13. The blood reservoir of claim 2, wherein the separator compresses a portion of the depth filter material against the support structure.

14. The blood reservoir of claim 2, further including a lower inner defoamer disposed within the second portion of the support structure and in fluid communication with the first blood inlet.

15. The blood reservoir of claim 14, wherein the lower inner defoamer is comprised of a portion of the outer defoamer, wrapped around the second end of the support structure and extending toward the separator.

16. The blood reservoir of claim 2, further including a dividing ledge located on the inside surface of the support structure between the first and second portions of the support structure, wherein the separator rests on the dividing ledge thereby substantially preventing blood from the second inlet mixing with blood from the first inlet before the blood from the second inlet passes through the depth filter.

17. The blood reservoir of claim 2, wherein the first and second blood inlets are located at the first end of the outer shell, wherein the separator has an opening, further including a tube in fluid communication with the first blood inlet and extending from the first end of the outer shell through the first portion of the support structure, through the opening in the separator and into the second portion of the support structure, wherein the tube is in fluid communication with the outer defoamer.

18. The blood reservoir of claim 17, further comprising a deflector having an opening, wherein the deflector is located between the first end of the support structure and the first end of the outer shell, wherein the tube extends through the opening of the deflector and is spaced apart from the deflector opening, wherein the deflector directs blood from the second inlet toward the depth filter.

19. The blood reservoir of claim 18, wherein the inner surface of the first end of the outer shell has an annular wall and wherein the deflector is disposed within the annular wall of the first end.

20. The blood reservoir of claim 19, wherein the deflector has an annular wall, wherein the first end of the support structure is located between the annular wall of the first end of the outer shell and the annular wall of the deflector.

21. The blood reservoir of claim 20, wherein the second end of the support structure abuts the second end of the outer shell.

22. An integrated cardiotomy and venous blood reservoir, comprising:
a hollow outer shell having a first end, a second end, and a wall extending from the first end to the second end;
a first blood inlet;
a second blood inlet;
a hollow shaped outer blood defoamer disposed within the outer shell and spaced apart from the wall of the outer shell, wherein the outer blood defoamer is in fluid communication with the first and second blood inlets;
a blood outlet in fluid communication with the outer blood defoamer;
a unitary, hollow support structure having a first end, a second end, a wall extending without interruption from the first to the second end, and an aperture within the wall, wherein the axial length of the support structure is comprised of a first portion and a second portion, wherein the first portion extends from the first end of the support structure along a portion of the axial length and the second portion extends the remaining portion of the axial length to the second end, and wherein the support structure is disposed within the outer defoamer;
a separator disposed within the support structure and located between the first and second portions of the support structure, wherein the first blood inlet is in fluid communication with the separator and second portion of the support structure;
a depth filter disposed within the first portion of the support structure, wherein the second blood inlet is in fluid communication with the depth filter, and wherein the depth filter is in fluid communication with the outer defoamer; and
a dividing ledge located on the inside surface of the support structure between the first and second portions of the support structure, wherein the separator rests on the dividing ledge thereby substantially preventing blood from the second inlet mixing with blood from the first inlet before the blood from the second inlet passes through the depth filter, wherein the separator further includes a first flange at one end and a second flange at the other end, wherein the dividing ledge further includes a plurality of bendable tabs, wherein the first flange rests on the dividing ledge and the bendable tabs are positioned between the first and second flanges to firmly maintain the separator in position between the first and second portions of the support structure.

23. An integrated cardiotomy and venous blood reservoir, comprising:
a hollow outer shell having a first end, a second end, and a wall extending from the first end to the second end;
a first blood inlet;
a second blood inlet;
a hollow shaped outer blood defoamer disposed within the outer shell and spaced apart from the wall of the outer shell, wherein the outer blood defoamer is in fluid communication with the first and second blood inlets;
a blood outlet in fluid communication with the outer blood defoamer;
a hollow support structure having a first end, a second end, a wall extending therebetween, and an aperture within the wall, wherein the axial length of the support structure is comprised of a first portion and a second portion, wherein the first portion extends from the first end of the support structure along a portion of the axial length and the second portion extends the remaining portion of the axial length to the second end, and wherein the support structure is disposed within the outer defoamer;
a separator disposed completely within the support structure and located between the first and second portions of the support structure, wherein the second portion is at least one-tenth the length of the first portion, wherein the first blood inlet is in fluid communication with the separator and second portion of the support structure; and
a depth filter disposed within the first portion of the support structure, wherein the second blood inlet is in fluid communication with the depth filter, and wherein the depth filter is in fluid communication with the outer defoamer.

24. The blood reservoir of claim 23, wherein the support structure is comprised of a cage having a plurality of ribs extending along the axial length of the support structure.

25. The blood reservoir of claim 23, wherein the support structure is positioned within the depth filter and wherein the depth filter surrounds the first portion of the support structure.

26. The blood reservoir of claim 23, wherein the outer defoamer and depth filter are disposed within the support structure.

27. The blood reservoir of claim 23, wherein the outer shell, outer blood defoamer, support structure, and depth filter have a generally, cylindrical shape.

28. The blood reservoir of claim 23, wherein the depth filter is hollow and the depth filter and first portion of the support structure are tapered at the end adjacent to the separator.

29. The blood reservoir of claim 23, wherein the outer shell, including first end, second end, and outer shell wall are formed from a plurality of transparent components coupled together.

30. The blood reservoir of claim 23, further including an inner defoamer disposed within the depth filter and in fluid communication with the second blood inlet and a lower inner defoamer disposed within the second portion of the support structure and in fluid communication with the center tube.

31. The blood reservoir of claim 23, further including a dividing ledge located on the inside surface of the support structure between the first and second portions of the support structure, wherein the separator rests on the dividing ledge thereby substantially preventing blood from the second inlet mixing with blood from the first inlet before the blood from the second inlet passes through the depth filter.

32. The blood reservoir of claim 23, wherein the first and second blood inlets are located at the first end of the outer shell, wherein the separator has an opening, and further including a tube in fluid communication with the first blood inlet and extending from the first end of the outer shell through the first portion of the support structure, through the opening in the separator and into the second portion of the support structure, wherein the tube is in fluid communication with the outer defoamer.

33. A method of assembling an integrated cardiotomy and venous blood reservoir, comprising the steps of:

providing a generally cylindrical, hollow support structure having a first end, a second end, and a wall therebetween with apertures, wherein the length of the support structure is comprised of a first portion extending from the first end and a portion of the axial length and a second portion extending the remaining portion of the axial length to the second end;

inserting the support structure within a generally cylindrical, hollow outer defoamer;

inserting a generally cylindrical, hollow depth filter within the first portion of the support structure;

inserting a separator within the depth filter located in the first portion of the support structure so the separator is located between the first and second portions of the support structure;

providing a generally cylindrical, hollow outer shell having a first end, a second end, a generally cylindrical wall therebetween, first blood inlet, second blood inlet, and blood outlet;

placing the support structure, including outer defoamer, filter, and separator, within the outer shell.

34. The method of claim 33, wherein no bonding agents are used to assemble and maintain in place the support structure, separator, depth filter and outer defoamer.

35. The method of claim 33, wherein the first portion of the support structure and the depth filter are tapered at one end, thereby making it easier to insert the depth filter into the support structure and the separator into the depth filter.

36. The method of claim 33, wherein the separator has an opening, further comprising the steps of:

placing a tube through the first portion of the support structure and through the opening in the separator so the tube extends along the axial length of the second portion of the support structure and is in fluid communication with the outer defoamer; and affixing the tube to the first blood inlet so that the tube is in fluid communication with the first blood inlet.

37. The method of claim 33, wherein the second end of the outer shell is open and wherein the separator has an opening, further comprising the steps of:

providing a cover having a first blood inlet and a second blood inlet;

providing a tube in fluid flow communication with the first blood inlet;

inserting the tube through the first portion of the support structure, through the opening in the separator, wherein the tube extends into the second portion of the support structure;

affixing the cover, with tube and support structure attached thereto, to the second end of the outer shell.

38. The method of claim 37, further comprising the step of attaching a deflector having an opening to the cover, wherein the tube extends through the opening in the deflector into the support structure.

39. The method of claim 33, wherein the inner surface of the support structure has a dividing ledge, and wherein the separator is positioned against the dividing ledge when inserted into the support structure.

40. The method of claim 39, wherein the depth filter is positioned against the dividing ledge and wherein the separator is inserted through the depth filter and positioned against the dividing ledge thereby compressing an end of the depth filter against the support structure.

* * * * *